United States Patent
Hadfield

(10) Patent No.: US 11,097,082 B2
(45) Date of Patent: Aug. 24, 2021

(54) DISCONTINUOUS CATHETER

(71) Applicant: INVENTASE LLC, Potsdam, NY (US)

(72) Inventor: Matthew J. Hadfield, Farmington, CT (US)

(73) Assignee: Inventase LLC, Potsdam, NY (US)

( * ) Notice: Subject to any disclaimer, the term of this patent is extended or adjusted under 35 U.S.C. 154(b) by 220 days.

(21) Appl. No.: 16/121,874

(22) Filed: Sep. 5, 2018

(65) Prior Publication Data

US 2019/0070388 A1 Mar. 7, 2019

Related U.S. Application Data

(60) Provisional application No. 62/554,048, filed on Sep. 5, 2017.

(51) Int. Cl.
*A61M 25/00* (2006.01)

(52) U.S. Cl.
CPC .... *A61M 25/0029* (2013.01); *A61M 25/0017* (2013.01); *A61M 25/0041* (2013.01); *A61M 25/0074* (2013.01); *A61M 2206/14* (2013.01)

(58) Field of Classification Search
CPC .......... A61M 25/0029; A61M 25/0017; A61M 25/0074; A61M 25/0041
See application file for complete search history.

(56) References Cited

U.S. PATENT DOCUMENTS

| | | | | |
|---|---|---|---|---|
| 3,769,981 A * | 11/1973 | McWhorter | ...... | A61M 25/0017 604/102.03 |
| 6,090,069 A | 7/2000 | Walker | | |
| 7,544,201 B2 * | 6/2009 | Pepper | ...... | A61M 25/0052 604/103 |
| 8,029,494 B2 | 10/2011 | Dua et al. | | |
| 8,684,963 B2 * | 4/2014 | Qiu | ...... | A61M 25/0026 604/96.01 |
| 2013/0253479 A1 * | 9/2013 | Su | ...... | A61L 29/041 604/544 |
| 2015/0273120 A1 | 10/2015 | Zamarripa et al. | | |
| 2015/0366462 A1 | 12/2015 | Ramos et al. | | |
| 2017/0348507 A1 * | 12/2017 | Erbey, II | ...... | A61M 25/0017 |
| 2019/0374754 A1 * | 12/2019 | Messenger | ...... | A61M 39/0208 |

OTHER PUBLICATIONS

Young, Lee W., "PCT International Search Report", dated Nov. 26, 2018 for application No. PCT/US18/49538, United States Patent and Trademark Office, Alexandria, Virginia.

Young, Lee W., "Written Opinion of the International Searching Authority", dated Nov. 26, 2018 for application No. PCT/US18/49538, United States Patent and Trademark Office, Alexandria, Virginia.

* cited by examiner

*Primary Examiner* — Tatyana Zalukaeva
*Assistant Examiner* — Jessica R Arble
(74) *Attorney, Agent, or Firm* — Woods Oviatt Gilman LLP; Dennis B. Danella, Esq.

(57) ABSTRACT

A urinary catheter passes from outside the body, through a urethra and into a bladder. The catheter includes an elongated tube having a distal end, proximal end, an intermediate length therebetween, and at least two lumens extending therein. The first lumen receives an inflation fluid at the distal end to inflate a balloon located at the proximal end of the catheter located within the bladder. The second lumen is discontinuous along at least a portion of the intermediate length and causes urine entering the second lumen from the bladder to contact a portion of the urethra before the urine is collected at the distal end of the catheter.

7 Claims, 2 Drawing Sheets

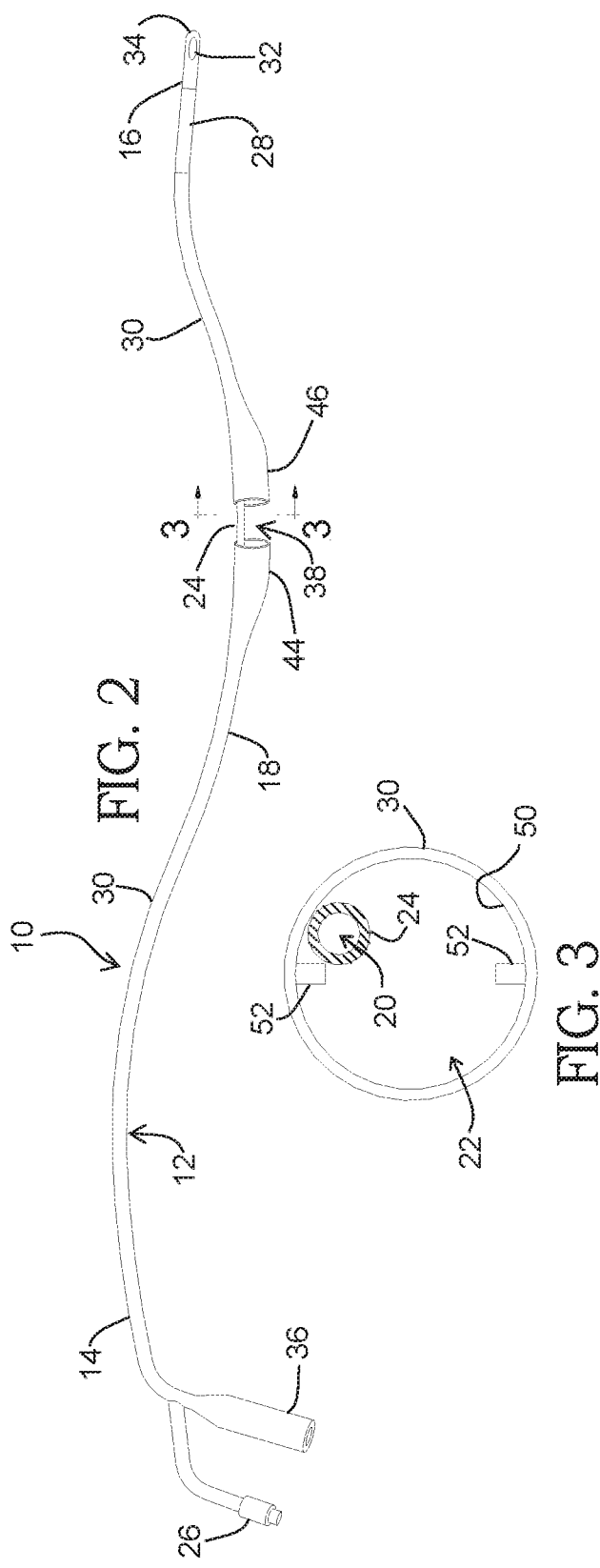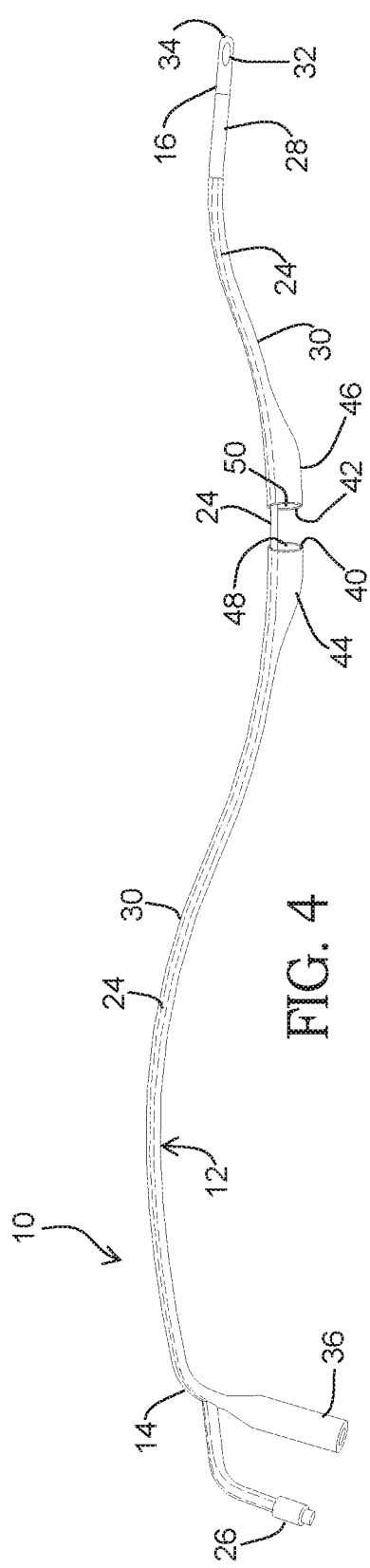

DISCONTINUOUS CATHETER

CROSS-REFERENCE TO RELATED APPLICATIONS

This application claims the benefit of U.S. Provisional Patent Application No. 62/554,048 filed Sep. 5, 2017, and entitled "Discontinuous Catheter", the contents of which are fully incorporated by reference herein.

FIELD OF THE INVENTION

The present invention relates to a urinary catheter; more particularly, the present invention is directed to a urinary catheter having a multi-luminal construction; and more particularly to urinary catheter have a multi-luminal construction wherein the outer tube of the catheter has a discontinuous sidewall.

BACKGROUND OF THE INVENTION

Urinary catheters are necessary when an individual is unable to properly drain their bladder. Indwelling catheters (most commonly a Foley catheter) are used when catheterization is required for an extended period of time (weeks to months). With reference to FIG. 1, a prior art Foley catheter consists of a flexible tube which is threaded from outside of the body, through the urethra and into the bladder. The Foley catheter includes two lumens running the length of the tubing. One lumen is open at both ends such that urine within the bladder may pass through the lumen to an external collection device. The second lumen includes a balloon at the proximal end (the end of the tubing residing within the bladder) which is filled with sterile water so as to expand the balloon within the bladder and prevent withdrawal of the tubing from the urethra (FIG. 1A).

One significant drawback to the use of Foley catheters is the risk for a bacterial infection, particularly a bladder infection commonly referred to as a catheter associated urinary track infection (CAUTI). Normally, the normal flow of sterile urine through the urethra prevents migration of bacteria up the urethra to the bladder. However, when a catheter is in place, the flow of urine within the urethra is bypassed with all urine traveling within and through the catheter lumen. As a result, bacteria may migrate along the outer surface of the catheter tubing and/or inner wall of the urethra. The risk of infection also increases if proper sterilization/hygiene is not adhered to during catheter insertion or while the catheter is in place.

Accordingly, there exists a need for a urinary catheter which eliminates or reduces the possibility of a bacterial infection during prolonged use. The present invention fills these and other needs.

SUMMARY OF THE INVENTION

The present invention is directed to a urinary catheter which passes from outside the body, through a urethra and into a bladder. The catheter includes an elongated tube having a distal end, proximal end, an intermediate length therebetween, and at least two lumens extending therein. The first lumen receives an inflation fluid at the distal end to inflate a balloon located at the proximal end of the catheter located within the bladder. The second lumen is discontinuous along at least a portion of the intermediate length and causes urine entering the second lumen from the bladder to contact a portion of the urethra before the urine is recollected by the catheter and delivered to the distal end of the catheter.

In another aspect, the discontinuous portion is at least one inch (2.54 cm) in length. The discontinuous portion may also be defined by opposing first and second tubing sidewalls, wherein the tube proximate each tubing sidewall is adapted to form a seal against an inner wall of the urethra. An inner surface of the second lumen proximate at least one of the first and second tubing sidewalls may also include one or more corrugations.

BRIEF DESCRIPTION OF THE DRAWINGS

The accompanying drawings form a part of the this specification and are to be read in conjunction therewith, wherein like reference numerals are employed to indicate like parts in the various views, and wherein:

FIG. 2 is a plan view of an embodiment of a urinary catheter in accordance with an aspect of the present invention;

FIG. 3 is cross section view of the urinary catheter of FIG. 2, shown generally along line 3-3 in FIG. 2; and FIG. 4 is a phantom view of the urinary catheter of FIG. 2 with the first lumen shown in dotted lines.

DETAILED DESCRIPTION OF THE INVENTION

Figure 1:
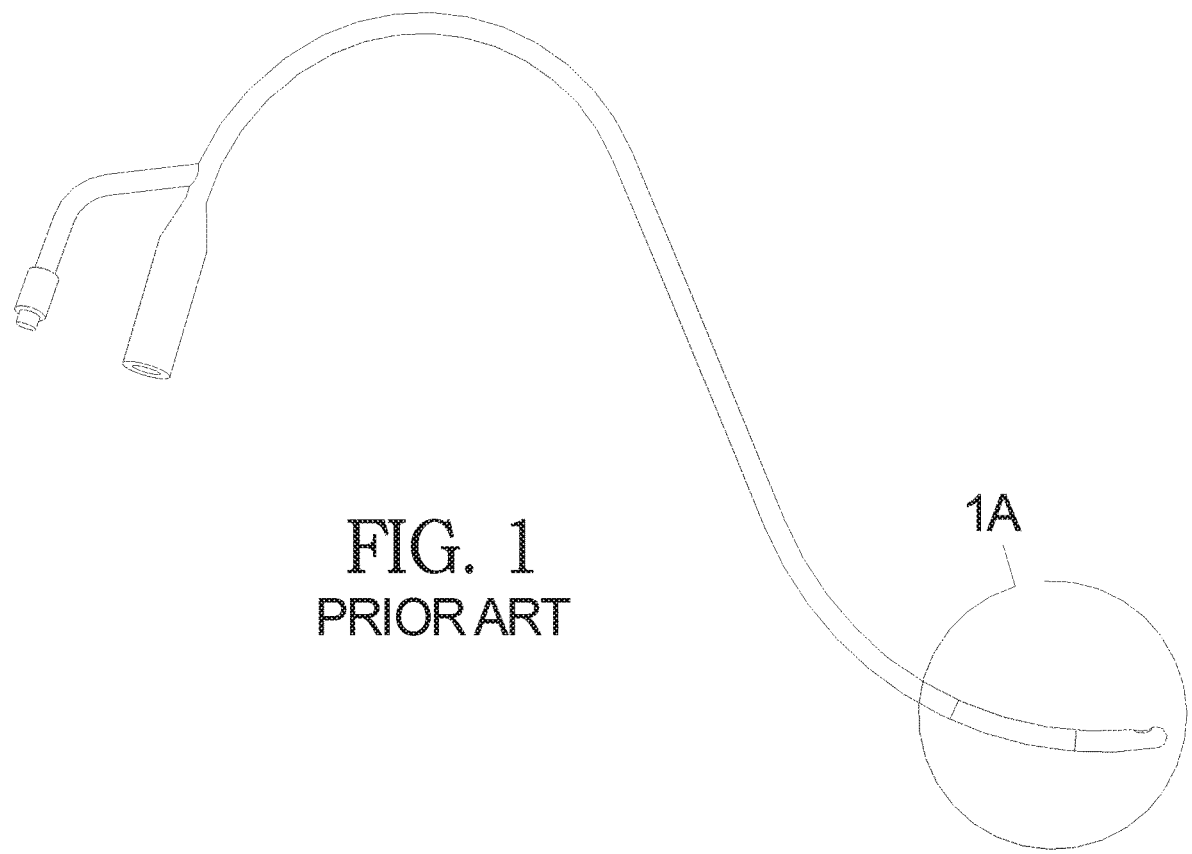
FIG. 1 is a plan view of a prior art urinary catheter.
Figure 1A:
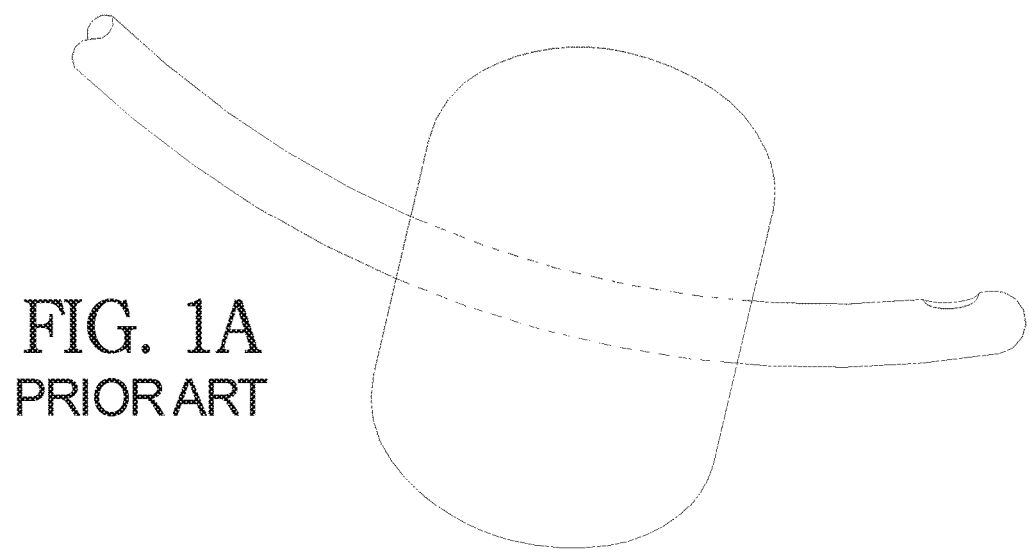
FIG. 1A is an expanded view of the proximal end of the prior art urinary catheter shown in FIG. 1 showing the balloon inflated.

Referring now to the drawings in detail, and specifically to FIGS. 2 through 4, a discontinuous catheter in accordance with an aspect of the present invention is generally indicated by reference numeral 10. Catheter 10 is comprised of an elongated tube 12 having a distal end 14, proximal end 16 and intermediate length 18 therebetween. Catheter 10 is a multi-luminal catheter, and in accordance with an aspect of the present invention, may include two lumens 20, 22.

As shown most clearly in FIG. 4, first lumen 20 is defined by a continuous tube wall 24 which extends from fluid port 26 at distal end 14 to a balloon 28 located near proximal end 16. In this manner, a fluid (such as sterile saline) may be injected at fluid port 26 and pass through first lumen 20 to expand balloon 28 when proximal end 16 is located within a patient's bladder so as to secure catheter 10 within the patient's urethra for draining of urine from the bladder.

Discontinuous tube wall 30 defines second lumen 22. Second lumen 22 includes an orifice 32 located near the terminus 34 of proximal end 16. As a result, urine within the bladder may enter second lumen 22 through orifice 32 where it may travel downstream to a urine collection port 36 located at distal end 14 of catheter 10. In accordance with an aspect of the present invention, second lumen 22 is discontinuous along at least one gap portion 38 of intermediate length 18 of catheter 10. With reference to FIG. 4, gap portion 38 may be defined by opposing first and second tubing sidewalls 40, 42. Gap portion 38 may be any desired length, such as and without limitation thereto, about ¼ inch to about 2 inches (0.635 cm to 5.08 cm), and more preferably about 1 inch (2.54 cm).

In accordance with a further aspect of the present invention, one or both of tubing sidewalls 40, 42 may include a respective portion 44, 46 of discontinuous tube wall 30 that is expanded or may be expandable so as to have a larger diameter than the remainder of discontinuous tube wall 30.

Portions 44, 46 may form a seal against the inner wall of the urethra. In this manner, urine exiting the bladder may not back flow around catheter 10 due to portion 44 and may not leak around catheter 10 due to portion 46. Thus, all urine discharged from the bladder exits catheter 10 through collection port 36. This is important for those catheterizations where patient urine output is monitored and measured. In accordance with this aspect of the present invention, urine is able to exit catheter 10 along the length of gap portion 18 before being recollected through tube sidewall 42. As a result, the urine contacts and flushes the inner sidewall of the urethra, thereby minimizing or preventing migration of bacteria along the urethra and catheter 10 toward the patient's bladder. Consequently, the risk of CAUTI is mitigated.

In accordance with another aspect of the present invention, inner wall 48, 50 of tubing sidewalls 40, 42 may include one or more corrugations or projections 52 which are configured to induce non-laminar flow of urine through at least gap portion 38 (FIG. 3). Non-laminar flow of urine through gap portion 38 may further facilitate flushing of the inner wall of the urethra, thereby further mitigating risk of bacterial infection of the bladder.

The foregoing description of the preferred embodiment of the invention has been presented for the purpose of illustration and description. It is not intended to be exhaustive nor is it intended to limit the invention to the precise form disclosed. It will be apparent to those skilled in the art that the disclosed embodiments may be modified in light of the above teachings. The embodiments described are chosen to provide an illustration of principles of the invention and its practical application to enable thereby one of ordinary skill in the art to utilize the invention in various embodiments and with various modifications as are suited to the particular use contemplated. Therefore, the foregoing description is to be considered exemplary, rather than limiting, and the true scope of the invention is that described in the following claims.

The invention claimed is:

1. A urinary catheter configured to pass from outside a human body, through a urethra and into a bladder, the catheter comprising:
    an elongated tube having a distal end, a proximal end, an intermediate length between the distal end and the proximal end; and
    at least two lumens defined in the elongated tube, wherein the at least two lumens includes a first lumen and a second lumen,
    wherein the first lumen is configured to receive an inflation fluid at the distal end to inflate a balloon located at the proximal end of the elongated tube located within the bladder, and
    wherein the second lumen is discontinuous along at least a portion of the intermediate length to form a discontinuous portion that is configured to cause urine entering the second lumen from the bladder to contact a portion of the urethra before the urine is collected at the distal end of the elongated tube,
    wherein the discontinuous portion is defined by opposing and adjacent first and second tubing sidewalls forming respective expanded sidewall portions, wherein the first tubing sidewall is not directly connected to the second tubing sidewall, and
    wherein the expanded sidewall portions include a first diameter that is greater than a second diameter of a remainder of the second lumen, and wherein each of the expanded sidewall portions are adapted to form a seal against an inner wall of the urethra.

2. The urinary catheter of claim 1, wherein the discontinuous portion is at least one inch (2.54 cm) in length.

3. The urinary catheter of claim 1, wherein an inner surface of the second lumen proximate at least one of the first and second tubing sidewalls includes one or more corrugations.

4. A urinary catheter configured to pass from outside a human body, through a urethra and into a bladder, the catheter comprising:
    a first tube defining a first lumen, wherein the first lumen is configured to receive an inflation fluid to inflate a balloon located within the bladder; and
    a second tube defining a second lumen, wherein the second lumen is larger than the first tube whereby the first tube is received within the second tube;
    wherein the second tube is discontinuous along a portion of its length whereby urine entering the second lumen from the bladder contacts the urethra,
    wherein the discontinuous portion of the second tube is defined by opposing and adjacent first and second tubing sidewalls forming respective expanded sidewall portions, wherein the first tubing sidewall is not directly connected to the second tubing sidewall, and
    wherein the expanded sidewall portions include a first diameter that is greater than a second diameter of a remainder of the second tube, and wherein each of the expanded sidewall portions are adapted to form a seal against an inner wall of the urethra.

5. The urinary catheter of claim 4, wherein the discontinuous portion of the second tube is at least one inch (2.54 cm) in length.

6. The urinary catheter of claim 4, wherein an inner surface of the second tube proximate at least one of the first and second tubing sidewalls includes one or more corrugations.

7. The urinary catheter of claim 4, wherein a longitudinal axis of the first tube is parallel to and not coaxial with a longitudinal axis of the second tube.

* * * * *